US012778487B2

(12) United States Patent
Turgeman et al.

(10) Patent No.: US 12,778,487 B2
(45) Date of Patent: Nov. 3, 2026

(54) POINT OF INTEREST (POI) MAP FOR CARDIAC ARRHYTHMIA DIAGNOSIS

(71) Applicant: BIOSENSE WEBSTER (ISRAEL) LTD., Yokneam (IL)

(72) Inventors: Aharon Turgeman, Zichron Ya'acov (IL); Shiran Eliyahu, Yokneam Illit (IL); Benjamin Cohen, Haifa (IL); Natan Sharon Katz, Atlit (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 272 days.

(21) Appl. No.: 18/500,441

(22) Filed: Nov. 2, 2023

(65) Prior Publication Data

US 2024/0180475 A1 Jun. 6, 2024

Related U.S. Application Data

(60) Provisional application No. 63/429,272, filed on Dec. 1, 2022.

(51) Int. Cl.
*A61B 5/367* (2021.01)
*A61B 5/343* (2021.01)

(52) U.S. Cl.
CPC .............. *A61B 5/367* (2021.01); *A61B 5/343* (2021.01)

(58) Field of Classification Search
CPC ......... A61B 5/367; A61B 5/343; A61B 5/339; A61B 5/743
See application file for complete search history.

(56) References Cited

U.S. PATENT DOCUMENTS 5,391,199 A 2/1995 Ben-haim
5,443,489 A 8/1995 Ben Haim
(Continued)

FOREIGN PATENT DOCUMENTS

EP 3750478 A1 12/2020
EP 4062833 A1 9/2022
JP 2001061789 A 3/2001

OTHER PUBLICATIONS

Seitz J, Bars C, Théodore G, Beurtheret S, Lellouche N, Bremondy M, Ferracci A, Faure J, Penaranda G, Yamazaki M, Avula UM, Curel L, Siame S, Berenfeld O, Pisapia A, Kalifa J. AF Ablation Guided by Spatiotemporal Electrogram Dispersion Without Pulmonary Vein Isolation: A Wholly Patient-Tailored Approach. J Am Coll Cardiol. Jan. 24, 2017;69(3):303-321. doi: 10.1016/j.jacc.2016.10.065. PMID: 28104073; PMCID: PMC5568427.
(Continued)

*Primary Examiner* — George R Evanisko
(74) *Attorney, Agent, or Firm* — Clayton, McKay & Bailey, PC

(57) ABSTRACT

A system includes a display and a processor. The processor is configured to receive a cardiac anatomical surface, and to receive multiple electrophysiological (EP) data points comprising (i) respective locations on the cardiac anatomical surface and (ii) respective values of arrhythmia-indicative EP parameters at the locations, and apply respective criteria to the values of the EP data points. For each EP data point whose value meets a respective criterion, the processor is configured to graphically encode the EP data point to generate a point of interest (POI), superimpose POIs of at least two types of arrhythmia-indicative EP parameters on the anatomical surface as to generate a POI map reflecting surface locations likely of being arrhythmogenic, and visualize the POI map to a user, on the display.

10 Claims, 4 Drawing Sheets

(56) References Cited

U.S. PATENT DOCUMENTS

| | | | | |
|---|---|---|---|---|
| 5,558,091 | A | 9/1996 | Acker | |
| 6,172,499 | B1 | 1/2001 | Ashe | |
| 6,239,724 | B1 | 5/2001 | Doron | |
| 6,301,496 | B1 * | 10/2001 | Reisfeld | A61B 5/287 600/407 |
| 6,332,089 | B1 | 12/2001 | Acker | |
| 6,484,118 | B1 | 11/2002 | Govari | |
| 6,618,612 | B1 | 9/2003 | Acker | |
| 6,690,963 | B2 | 2/2004 | Ben Haim | |
| 6,788,967 | B2 | 9/2004 | Ben Haim | |
| 6,892,091 | B1 | 5/2005 | Ben Haim | |
| 7,536,218 | B2 | 5/2009 | Govari | |
| 7,756,576 | B2 | 7/2010 | Levin | |
| 7,848,787 | B2 | 12/2010 | Osadchy | |
| 7,869,865 | B2 | 1/2011 | Govari | |
| 8,456,182 | B2 | 6/2013 | Bar-Tal | |
| 10,624,557 | B2 * | 4/2020 | Li | A61B 5/0536 |
| 11,160,485 | B2 | 11/2021 | Botzer | |
| 2009/0192393 | A1 | 7/2009 | Hayam et al. | |
| 2009/0193393 | A1 | 7/2009 | Baldwin | |
| 2022/0211314 | A1 | 7/2022 | Govari | |

OTHER PUBLICATIONS

International Search Report for corresponding PCT Appln. No. PCT/IB2023/061773 dated Feb. 6, 2024.

* cited by examiner

POINT OF INTEREST (POI) MAP FOR CARDIAC ARRHYTHMIA DIAGNOSIS

CROSS-REFERENCE TO RELATED APPLICATIONS

This application claims the benefit of U.S. Provisional Patent Application 63/429,272, filed Dec. 1, 2022, whose disclosure is incorporated herein by reference.

FIELD OF THE DISCLOSURE

The present disclosure relates generally to cardiac electrophysiological (EP) mapping, and particularly to cardiac EP maps.

BACKGROUND OF THE DISCLOSURE

EP maps generated from catheter-acquired EP signals were previously described in the patent literature. For example, U.S. Patent Application Publication 2022/0211314 describes a method including receiving (i) a modeled surface of at least a portion of a heart and (ii) multiple EP values measured at multiple respective positions in the heart. Multiple regions are defined on the modeled surface and, for each region, a confidence level is estimated for the EP values whose positions fall in the region. The modeled surface is presented to a user, including (i) the EP values overlaid on the modeled surface, and (ii) the confidence level graphically visualized in each region of the modeled surface.

As another example, U.S. Pat. No. 11,160,485 describes a method including storing an anatomical map of at least a portion of a surface of a heart. Respective electrogram (EGM) signal amplitudes measured at respective positions on the surface of the heart are stored. Based on the EGM signal amplitudes, defined are: one or more first regions of the surface in which the EGM signal amplitudes are fractionated, and one or more second regions of the surface in which the EGM signal amplitudes are non-fractionated. A first surface representation is generated for the fractionated EGM signal amplitudes in the first regions. Propagation times are extracted from the non-fractionated EGM signal amplitudes in the second regions, and a second surface representation of the propagation times is derived.

The first and second surface representations of the respective first and second regions of the surface are simultaneously presented, overlaid on the anatomical map. Julien S. et al describe in a paper titled, “Atrial Fibrillation (AF) Ablation Guided by Spatiotemporal Electrogram Dispersion Without Pulmonary Vein Isolation,” JACC. Vol. 69, No. 3, (2017), how to identify with EP mapping clustering of intracardiac electrograms exhibiting spatiotemporal dispersion is indicative of AF drivers.

The present disclosure will be more fully understood from the following detailed description of the examples thereof, taken together with the drawings in which:

DETAILED DESCRIPTION OF EXAMPLES

Overview

Figure 1:
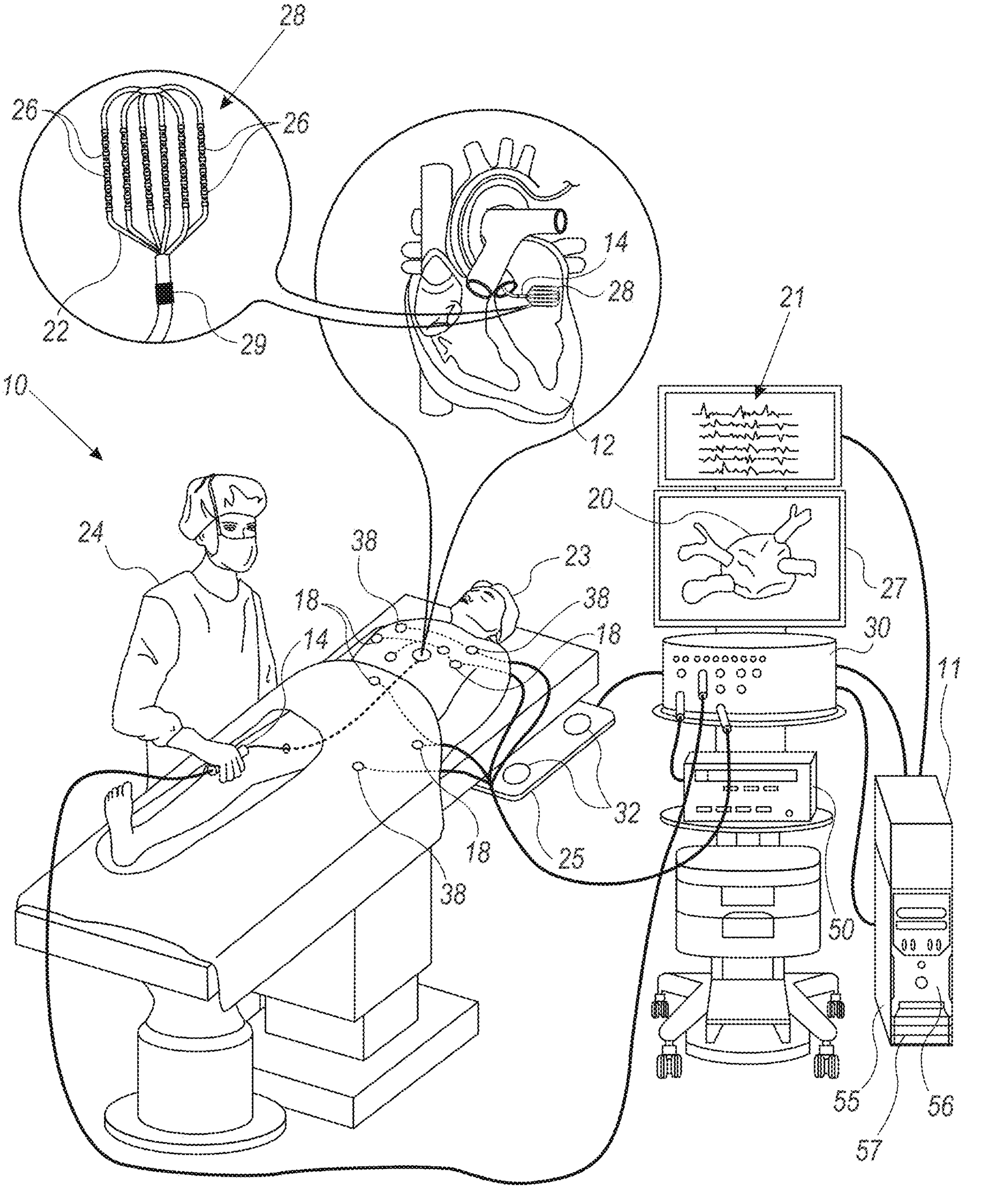
FIG. 1 is a schematic, pictorial illustration of a catheter-based electrophysiology (EP) mapping and ablation system, in accordance with an example of the present disclosure.

Probe-based (e.g., multi-electrode catheter-based) cardiac diagnostic and therapeutic systems may measure a large number of intra-cardiac electrophysiological (EP) signals, such as electrograms (EGM), during an invasive procedure. Typically, the analysis of such a vast amount of EP information is facilitated by generating and presenting to a user (e.g., a physician or a clinical application specialist) one or more EP maps. Each such EP map can display typical EP parameters for the procedure. Examples of EP parameters that may be presented include the arrhythmia-indicative EP parameters selected from a list comprising cycle length, regional ripple percentage, local activation time (LAT), bipolar potential, activation wave velocity, and complex fractionated atrial electrograms (CFAE).

A physician performing diagnosis and/or planning a treatment for cardiac arrhythmia typically flips between the different EP maps to examine a variety of cardiac tissue properties. Thus, diagnosis and planning (e.g., selection of an ablation location to eliminate an arrhythmia) are typically based on mental compilation of information from a plurality of EP maps, each displaying of one or more of the aforementioned EP parameters. The physician flipping between the different EP maps may get lost in details and confusing indications, and thus may not be able to prioritize tissue locations for treatment.

Examples of the present disclosure that are described herein provide algorithms and visualizations for high-level and fully automated acquisition and/or selection of EP data points for display.

In some examples, a user or a processor sets acquisition criteria, to acquire only data points that meet these criteria for use in analysis. Such criteria include stability of acquisition for a minimal predefined duration of time (e.g., 2.5 Seconds) for a minimum predefined number of electrodes (e.g., a group of electrodes that covers a minimal contiguous tissue area at once) of the multi-electrode catheter.

The disclosed techniques may use a GUI to select several types of EP parameters and respective criteria applied to the acquired data points. Using the EP selection, a processor analyzes and displays points of interest (POI) maps, as will be described below. Using one or more of the disclosed POI maps, the physician may overcome, for example, the above-described difficulties in prioritizing tissue locations for ablation.

In some examples, a processor displays an anatomical map overlayed with graphically encoded (e.g., flagged) POIs. To this end, the processor receives multiple EP data points comprising respective locations on the cardiac anatomical surface, and respective values of arrhythmia-indicative EP parameters at the locations.

The processor applies respective criteria to the values of the EP data points. For each EP data point whose value meets a respective criterion, the processor graphically encodes the EP data point to generate a point of interest (POI).

The processor superimposes POIs of at least two types of arrhythmia-indicative EP parameters on the anatomical surface as to generate a POI map reflecting surface locations likely of being arrhythmogenic, and visualize the POI map to a user, on the display.

In one example, to reflect surface locations likely being arrhythmogenic, the processor divides the cardiac anatomical surface into unit areas of predefine size and shape, and per each unit area, or given portion of the unit areas, determines a count of differently encoded POIs therein, and graphically indicate the count at the unit area.

A graphical indication (e.g., a flag) may be shaped and/or color-coded to indicate the EP parameter that it represents. The disclosed POI map does not indicate the value of each of the EP parameters, only the location in the anatomical map at which the EP parameter value meets a criterion. With the disclosed POI maps, tissue that shows arrhythmogenic behavior may be flagged by multiple flags, or by a special flag indicative of multiple flags.

The flag may be a pin or a mosaic of colors on the anatomical map. The graphical indication may be embedded in the surface itself, such as in wavefronts that are displayed using a continuous color code, as done, for example, with coherent EP maps, and with spatiotemporal dispersion maps. The anatomical map may be a modeled map (fast anatomical map, FAM) or a 3D image of a portion of the heart.

In this way the physician may get an overview of POIS on the anatomical map. As noted above, the processor may divide the anatomical maps into unit areas of predefined size and shape, and, in each unit area, generate from different flags of different EP parameters a combined flag indicative of the multiple flags therein. For example, if the flags are stripes of different colors, the processor may generate therein a complex stripe pattern representative of the different colors.

In one example of a POI map, the processor displays an EP map, such as a spatial-temporal dispersion map (sequential activation of consecutive bipolar of multielectrode catheter spanning more than 85% (70-90%) of has max derivative above defined threshold of the atrial fibrillation cycle length) over which the processor adds protruding color-coded pins to indicate additional parameters of interest for the arrhythmia. Specifically, the processor may generate this way a POI map of atrial fibrillation (AFib) that will assist the physician in determining where to ablate tissue. A user may alter the height and/or width of the pins depending on the criterion they are selected to represent.

An example scheme for color-coding protruding pins follows:

- Red pins for locations with regularity in cycle-length defined, for example, as points within a range of [minimum cycle-length, minimum cycle-length+10 ms]
- Blue pins for locations with regularity in STD cycle-length defined, for example, as points with STD in a range of [minimum STD cycle-length, minimum STD cycle-length+5 ms]
- Brown pins for locations with points with CFAE (showing fractionated signals)
- Purple pins for locations with regional ripple percentage, the purple pins appearing on points with above 0.75*maximum regional ripple percentage In another example, a POI map is provided to a physician with a color scale that classifies areas according to the number of parameters that indicate an arrhythmia therein. A physician is able to choose from a list of parameters to be used to build the map. For example, the physician may choose five parameters. A scale on the map shows the number of these chosen parameters, e.g., ranging from 0 to 5, that affect a given region of the map. The physician may consider that regions showing a 5 are candidates for ablation.

The physician may choose different EP parameters from the list to be counted in the EP parameter scale. In addition, the physician may assign weights to the parameters.

Finally, a processor is used in training a machine-learning model with a sufficient number of POI maps to construct an expert application that can generates one or more optimized POI maps.

System Description

FIG. 1 is a schematic, pictorial illustration of a catheter-based electrophysiology (EP) mapping and ablation system 10, in accordance with an example of the present disclosure.

System 10 may include multiple catheters, which are percutaneously inserted by physician 24 through the patient's vascular system into a chamber or vascular structure of a heart 12. In the shown example, a delivery sheath catheter is inserted into the left or right atrium near a desired location in heart 12. Thereafter, a plurality of catheters can be inserted into the delivery sheath catheter so as to arrive at the desired location. The plurality of catheters may include catheters dedicated for sensing intracardiac electrogram (IEGM) signals, catheters dedicated for ablation and/or catheters dedicated for both sensing and ablation. An example EP mapping catheter 14 that is configured for sensing IEGM is illustrated herein. Physician 24 brings a distal tip 28 (also called hereinafter "distal end assembly 28") of catheter 14 into contact with the heart wall for sensing a target site in heart 12. For ablation, physician 24 similarly brings a distal end of an ablation catheter to a target site for ablation.

Catheter 14 is an exemplary catheter that includes one, and preferably multiple, electrodes 26 optionally distributed over a plurality of splines 22 at distal tip 28 and configured to sense IEGM signals. Catheter 14 may additionally include a position sensor 29 embedded in or near distal tip 28 for tracking position and orientation of distal tip 28. Optionally, and preferably, position sensor 29 is a magnetic-based position sensor including three magnetic coils for sensing three-dimensional (3D) position and orientation.

Magnetic-based position sensor 29 may be operated together with a location pad 25 that includes a plurality of magnetic coils 32 configured to generate magnetic fields in a predefined working volume. Real-time position of distal tip 28 of catheter 14 may be tracked based on magnetic fields generated with location pad 25 and sensed by magnetic-based position sensor 29. Details of the magnetic based position sensing technology are described in U.S. Pat. Nos. 5,539,199; 5,443,489; 5,558,091; 6,172,499; 6,239,724; 6,332,089; 6,484,118; 6,618,612; 6,690,963; 6,788,967; 6,892,091.

System 10 includes one or more electrode patches 38 positioned for skin contact on patient 23 to establish a location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182.

A recorder 11 displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more electrodes at a distal tip of a catheter configured for ablation. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or a combinations thereof.

Patient interface unit (PIU) 30 is an interface configured to establish electrical communication between catheters, electrophysiological equipment, power supply and a workstation 55 for controlling the operation of system 10. Electrophysiological equipment of system 10 may include, for example, multiple catheters, location pad 25, body surface ECG electrodes 18, electrode patches 38, ablation energy generator 50, and recorder 11. Optionally, and preferably, PIU 30 additionally includes processing capability for implementing real-time location computations of the catheters and for performing ECG calculations.

Workstation 55 includes memory 57, processor unit 56 with memory or storage with appropriate operating software loaded therein, and user interface capability. Workstation 55 may provide multiple functions, optionally including (1) modeling the endocardial anatomy in three-dimensions (3D) and rendering the model or a POI map 20 for display on a display device 27, (2) displaying on display device 27 activation sequences (or other data) compiled from recorded electrograms 21 in representative visual indicia or imagery included in the rendered POI map 20, (3) displaying real-time location and orientation of multiple catheters within the heart chamber, and (4) displaying on display device 27 sites of interest such as places where ablation energy has been applied. One commercial product embodying elements of system 10 is available as the CARTO™ 3 System, available from Biosense Webster, Inc., 31A Technology Drive, Irvine, CA 92618.

Points of Interest (POI) Cardiac Maps

Figure 2:
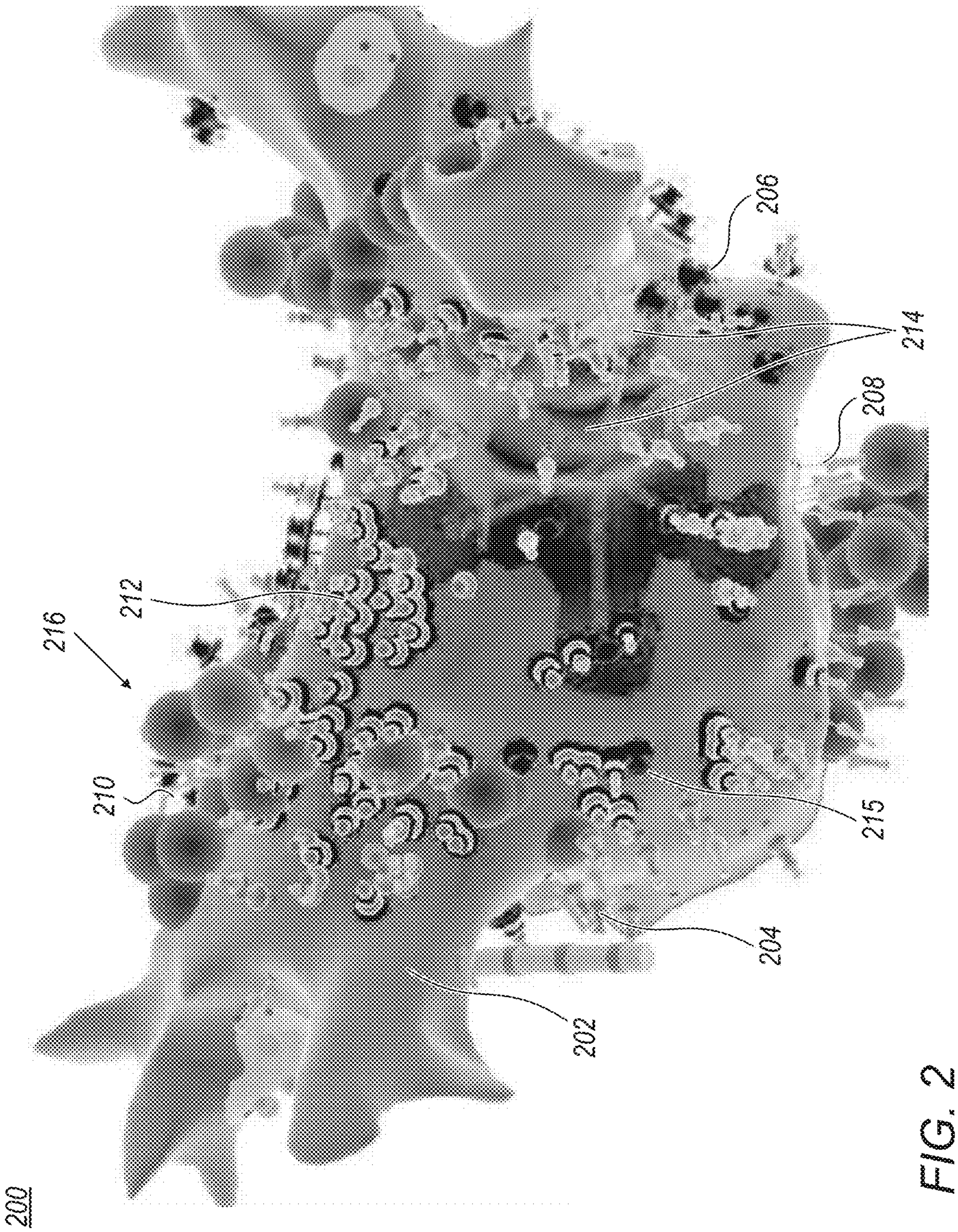
FIG. 2 is a schematic illustration of a points of interest (POI) map, in accordance with an example of the present disclosure.

FIG. 2 is a schematic illustration of a POI map 200, in accordance with an example of the present disclosure. POI map 200 may be the POI map 20 shown displayed in FIG. 1.

POI map 200 comprises an anatomical map 202, which, in the shown case, is of a left atrium. POI map 200 further comprises graphically encoded (e.g., flagged) EP data points. The data POIs are for given unit areas on the map superimposed by at least two EP parameters. The flags may be graphically shaped and/or color coded to indicate the parameter that they represent. The disclosed POI map does not indicate the value of each of the EP parameters, only the location in the anatomical map at which the EP parameter value crosses a threshold.

In the shown example of POI map 200, the processor displays protruding color-coded pins indicating additional parameters of interest for an arrhythmia such as atrial fibrillation (AFib).

An example of color-coded scheme for the protruding pins includes:

Red pins 204 for locations with regularity in cycle length defined, for example, as points within a range of [minimum cycle-length, minimum cycle-length+10 ms]

Blue pins 206 for locations with regularity in STD cycle length defined, for example, as points with STD in a range of [minimum STD cycle-length, minimum STD cycle-length+5 ms]

Brown pins 208 for locations with points with CFAE (showing fractionated signals)

Purple pins 210 for locations with regional ripple percentage, the purple pins appearing on points with above 0.75*maximum regional ripple percentage As further seen, pins 212 include different colored rings to mark locations where indications of pins 204, 206, and 208 overlap each other.

EP wavefronts may be color coded (214) on the map as well, as done, for example, with coherent EP maps.

One or more areas on the EP map can be graphically encoded (215), if the analysis shows the area demonstrates spatiotemporal dispersion above a given slope. Such dispersion can be determined if a sufficient number of electrodes cover an are under test for a sufficient time duration.

Finally, additional indicators may be included, such as balls 216, which are for example point Potential Duration (PM) bigger than a defined threshold.

Figure 3:
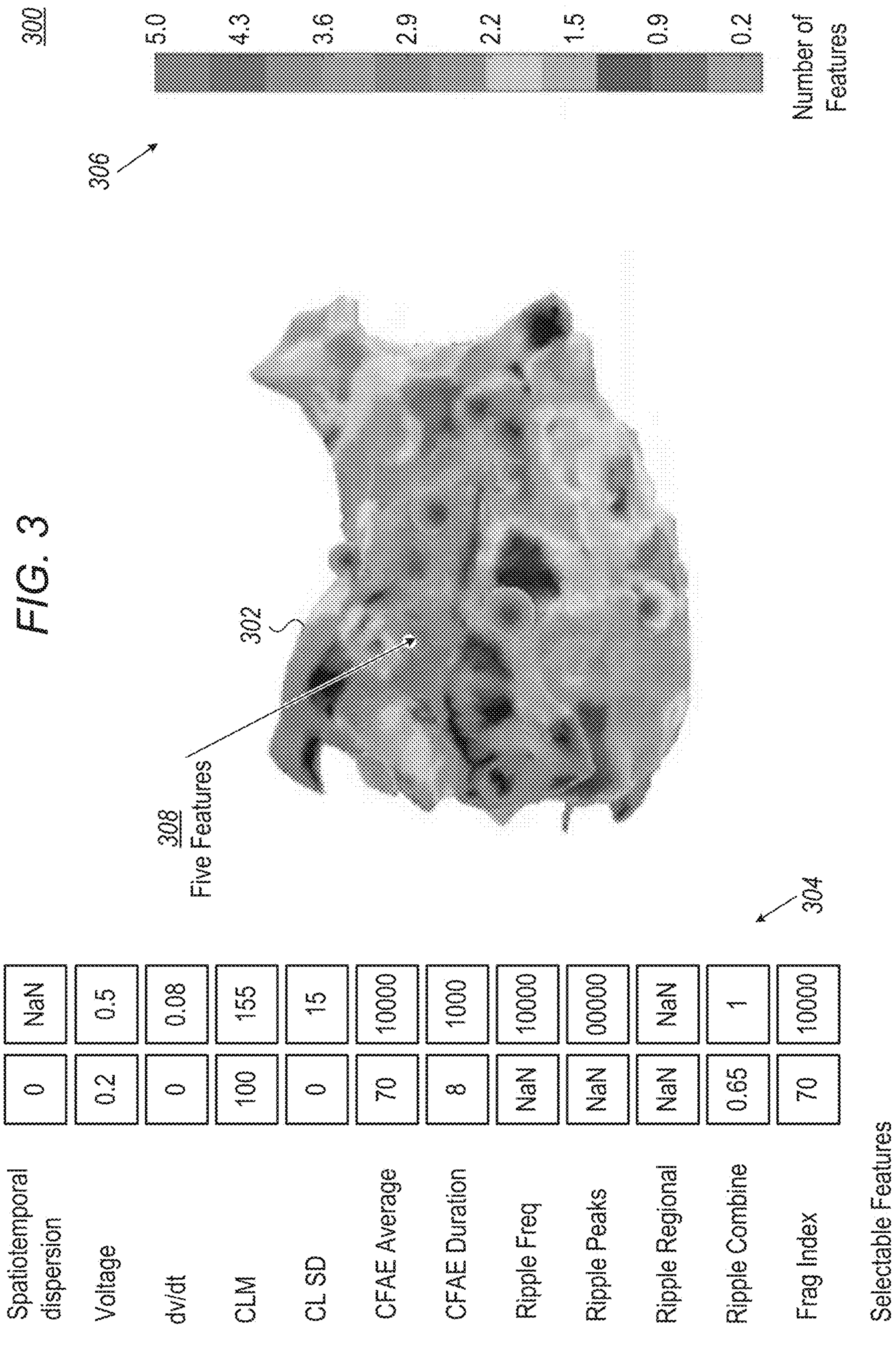
FIG. 3 is a schematic illustration of a POI map, in accordance with another example of the present disclosure.

FIG. 3 is a schematic illustration of a POI map 300, in accordance with another example of the present disclosure. POI map 300 may be the POI map 20 shown displayed in FIG. 1. POI map 300 comprises an anatomical map 302, which in the shown case is of a left atrium.

POI map 300 is provided to a physician with a color scale that classifies areas according to the number of EP parameters indicative of an arrhythmia. A physician is able to choose from a list 304 of EP parameters to be used to build POI map 300. For example, the physician may choose five EP parameters from a list of arrhythmia-indicative EP parameters such as the aforementioned cycle length, regional ripple percentage, local activation time (LAT), bipolar potential, activation wave velocity, spatiotemporal dispersion slope, and complex fractionated atrial electrograms (CFAE). A scale 306 on the map shows the number of these chosen EP parameters, e.g., ranging from 0 to 5, that affect a given region of the map. The physician may consider that regions 308 showing a 5 are candidates for ablation.

The physician may choose different EP parameters from list 304 to be counted in the EP parameter scale 306. In addition, the physician may assign weights to the EP parameters.

Figure 4:
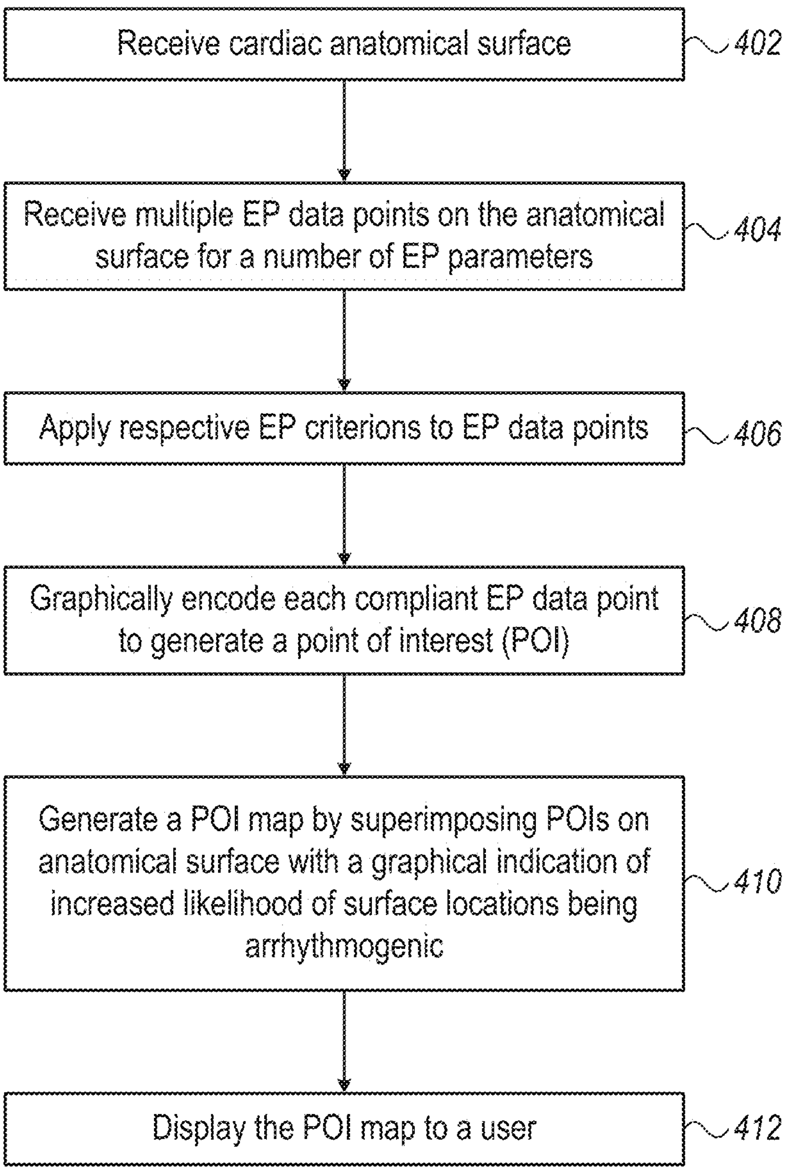
FIG. 4 is a flow chart that schematically illustrates a method for generating, editing and presenting a POI map, in accordance with an example of the present disclosure.

FIG. 4 is a flow chart that schematically illustrates a method for generating, editing and presenting a POI map, such as maps 200 and 300, in accordance with an example of the present disclosure. The algorithm, according to the presented example, carries out a process that begins with processor 28 receiving uploading) a cardiac anatomical surface, such as anatomical maps 202 and 302, at an anatomical surface uploading step 402.

Next, the processor receives multiple EP data points on the anatomical surface that correspond (belong) each to one of a number of EP parameters, at EP data points receiving step 404.

At criteria applying step 406, The processor applies to the EP data points respective (i.e., for each EP parameter) EP criteria. These may include EP values crossing thresholds or falling within ranges. The EP parameters may be taken from the aforementioned arrhythmia-indicative EP parameters of cycle length, regional ripple percentage, local activation time (LAT), bipolar potential, activation wave velocity, spatiotemporal dispersion slope, and complex fractionated atrial electrograms (CFAE).

At graphics step 408, the processor graphically encodes each EP data that complies with a criterion, so as to generate a point of interest.

At POI map generation step 410, the processor graphically indicates POIs in locations where at least two or more of the EP parameters meet respective predefined criteria (e.g., as seen in pins 212 of FIG. 2) and/or graphically indicate POIs according to a scale determining a count (e.g., up to 5 as seen in scale 306 of FIG. 3) of differently encoded POIs therein, and graphically indicate the count at the unit area. This way, the processor has the POI map providing an indication of surface locations likely to be arrhythmogenic.

Finally, the processor displays the POI map to a user, such as displaying map 20 on display device 27, at a POI map displaying step 412.

EXAMPLES

Example 1

A system (10) includes a display (27) and a processor (56). The processor is configured to receive a cardiac anatomical surface (202, 302), and to receive multiple electrophysiological (EP) data points comprising (i) respective locations on the cardiac anatomical surface and (ii) respective values of arrhythmia-indicative EP parameters at the locations, and apply respective criteria to the values of the EP data points. For each EP data point whose value meets a respective criterion, the processor is configured to graphically encode (204, 206, 208, 210, 212) the EP data point to generate a point of interest (POI), superimpose POIs of at least two types of arrhythmia-indicative EP parameters on the anatomical surface as to generate a POI map reflecting surface locations likely of being arrhythmogenic, and visualize the POI map to a user, on the display (27).

Example 2

The system (10) according to example 1, wherein the arrhythmia-indicative EP parameters are of types selected from a list comprising at least two of cycle-length, regional ripple percentage, local activation time (LAT), bi-polar potential, wave velocity, activation spatiotemporal dispersion slope, and complex fractionated atrial electrograms (CFAE).

Example 3

The system (10) according to any of examples 1 and 2, wherein the processor (56) is configured to visualize the POI map by dividing the cardiac anatomical surface (202, 302) into unit areas of predefined size and shape, and, per each unit area, determine a count of differently encoded (204, 206, 208, 210) POIs therein, and graphically indicate (306) the count at the unit area.

Example 4

The system according to any of examples 1 through 3, wherein, for a given unit area, the processor is configured to graphically indicate (204, 206, 208, 210) the count (306) by generating a new graphical indication reflecting the count of the differently graphically encoded POIs therein.

Example 5

The system according to any of examples 1 through 3, wherein, for a given unit area, the processor is configured to reflect the count (306) by combining the differently graphically encoded (204, 206, 208, 210) POIs into a single POI graphically encoded (212) to indicate each of the differently graphically encoded POIs therein.

Example 6

A method includes receiving a cardiac anatomical surface (202, 302). Multiple electrophysiological (EP) data points are received, each comprising (i) respective locations on the cardiac anatomical surface and (ii) respective values of arrhythmia-indicative EP parameters at the locations. Respective criteria are applied to the values of the EP data points. for each EP data point whose value meets a respective criterion, the EP data point is graphically encoded (204, 206, 208, 210, 212) to generate a point of interest (POI). POIs of at least two types of arrhythmia-indicative EP parameters are superimposed on the anatomical surface as to generate a POI map reflecting surface locations likely of being arrhythmogenic. The POI map is visualized to a user.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:

a display; and a processor, configured to:

receive data representing a cardiac anatomical surface;

receive multiple electrophysiological (EP) data points comprising (i) respective locations on the cardiac anatomical surface and (ii) respective values of arrhythmia-indicative EP parameters at the locations;

apply at least two types of arrhythmia-indicating criteria to the values of the EP data points;

for each of the EP data points whose value meets one or more of the arrhythmia-indicating criteria, graphically encode the EP data point to generate a point of interest (POI);

superimpose the POIs of at least two types of arrhythmia-indicative EP parameters on the anatomical surface to generate a POI map reflecting surface locations likely of being arrhythmogenic; and visualize the POI map to a user, on the display, by graphically indicating, for each of one or more regions of the cardiac anatomical surface, a count of different types of the arrhythmia-indicative EP parameters for which corresponding POIs are present in the region;

wherein the system is configured to apply ablation energy to cardiac tissue at a selected location based on the POI map.

2. The system according to claim 1, wherein the arrhythmia-indicative EP parameters are selected from a list comprising at least two of cycle-length, regional ripple percentage, local activation time (LAT), bi-polar potential, activation wave velocity, spatiotemporal dispersion slope, and complex fractionated atrial electrograms (CFAE).

3. The system according to claim 1, wherein the one or more regions comprise unit areas of predefined size and shape, and, for each unit area, the count of the different types of arrhythmia-indicative EP parameters for which corresponding POIs are present in the respective unit area is graphically indicated at the respective unit area.

4. The system according to claim 3, wherein, for a given unit area, graphically indicating the count comprises generating a new graphical indication reflecting the count of the different types of arrhythmia-indicative EP parameters for which corresponding POIs are present in the given unit area.

5. The system according to claim 3, wherein, for a given unit area, graphically indicating the count comprises combining the corresponding POIs present in the given unit area into a single POI graphically encoded to indicate the different types of arrhythmia-indicative EP parameters for which the corresponding POIs are present in the given unit area.

6. A method, comprising:

receiving data representing a cardiac anatomical surface;

receiving multiple electrophysiological (EP) data points comprising (i) respective locations on the cardiac anatomical surface and (ii) respective values of arrhythmia-indicative EP parameters at the locations;

applying at least two types of arrhythmia-indicating criteria to the values of the EP data points;

for each of the EP data points whose value meets one or more of the arrhythmia-indicating criteria, graphically encoding the EP data point to generate a point of interest (POI);

superimposing the POIs of at least two types of arrhythmia-indicative EP parameters on the anatomical surface to generate a POI map reflecting surface locations likely of being arrhythmogenic;

visualizing the POI map to a user, including graphically indicating, for each of one or more regions of the cardiac anatomical surface, a count of different types of the arrhythmia-indicative EP parameters for which corresponding POIs are present in the region; and applying ablation energy to cardiac tissue at a selected location based on the POI map.

7. The method according to claim 6, wherein the arrhythmia-indicative EP parameters are selected from a list comprising at least two of cycle-length, regional ripple percentage, local activation time (LAT), bi-polar potential, activation wave velocity, and complex fractionated atrial electrograms (CFAE).

8. The method according to claim 6, wherein the one or more regions comprise unit areas of predefined size and shape, and, for each unit area, the count of the different types of arrhythmia-indicative EP parameters for which corresponding POIs are present in the respective unit area is graphically indicated at the respective unit area.

9. The method according to claim 8, wherein, for a given unit area, graphically indicating the count comprises generating a new graphical indication reflecting the count of the different types of arrhythmia-indicative EP parameters for which corresponding POIs are present in the given unit area.

10. The method according to claim 8, wherein, for a given unit area, graphically indicating the count comprises combining the corresponding POIs present in the given unit area into a single POI graphically encoded to indicate the different types of arrhythmia-indicative EP parameters for which the corresponding POIs are present in the given unit area.

* * * * *